United States Patent [19]
Cavazza

[11] Patent Number: 6,066,664
[45] Date of Patent: *May 23, 2000

[54] METHOD FOR DECREASING THE APPETITE IN BULIMIC, OVERWEIGHT INDIVIDUALS

[75] Inventor: Claudio Cavazza, Rome, Italy

[73] Assignee: SIGMA-TAU Industrie Farmaceutiche Riunite S.p.A., Rome, Italy

[*] Notice: This patent issued on a continued prosecution application filed under 37 CFR 1.53(d), and is subject to the twenty year patent term provisions of 35 U.S.C. 154(a)(2).

[21] Appl. No.: 08/870,299

[22] Filed: Jun. 6, 1997

[51] Int. Cl.$^7$ .................................................. A01N 43/38
[52] U.S. Cl. ........................ 514/419; 514/546; 514/547; 514/552
[58] Field of Search ................................... 514/546, 547, 514/552, 419

[56] References Cited

U.S. PATENT DOCUMENTS 3,810,994   5/1974   Wiegand .................................. 424/316

OTHER PUBLICATIONS

Fletcher et al., "Dissociation of the anorectic action s of 5–HTP and fenfluramine", Psychopharmacology (Berlin), 89(2), pp. 216–220, 1986, see abstract; 1986.

P. Borum, "1$^{st}$. Meeting on Nutrition in Childhood, Carnitine's Biological Role in Childhood", Clinica Pediatrica V Istituto Di Scienze Biomediche Ospedale S. Paolo–Milano, Milano Nov. 27–28, 1986.

1991 David W. Smith Workshop on Malformations and Morphogenesis, "Prevalence of Lipid Storage Myopathy in the Macrocephaly Syndromes: Clinical Correlations and Outcome of Carnitine Therapy", Sep. 27–Oct. 1, 1991.

Clampagila et al, "Effect of L–carnitine of protein catabolic rate in chronic hemodialysis patients", Journal of The American Society of Nephrology, vol. 8, 1997.

Paul J. Fletcher et al, "Dissociation of the anorectic actions of 5–HTP and fenfluramine", Psychopharmacology, vol. 89, pp. 216–220, 1986.

*Primary Examiner*—Dwayne C. Jones
*Attorney, Agent, or Firm*—Oblon, Spivak, McClelland, Maier & Neustadt, P.C.

[57] ABSTRACT

A method for controlling and decreasing the appetite in an overweight individual is disclosed which comprises administering to said individual 5-hydroxytryptophan and an alkanoyl L-carnitine wherein the alkanoyl group has 2–6 carbons atoms, preferably acetyl L-carnitine, or a pharmacologically acceptable salt thereof.

6 Claims, No Drawings

METHOD FOR DECREASING THE APPETITE IN BULIMIC, OVERWEIGHT INDIVIDUALS

SUMMARY OF THE INVENTION

The present invention relates to a method for controlling and decreasing the appetite in overweight individuals and to 5-hydroxytryptophan (5-HTP)-containing anorectic pharmaceutical compositions.

According to its broadest aspect the invention relates to the coordinated use of 5-HTP with an alkanoyl L-carnitine wherein the alkanoyl group has 2–6 carbon atoms or a pharmacologically acceptable salts thereof. By "coordinated use" of the aforesaid compounds it is meant indifferently either the coadministration, i.e. the substantially concomitant supplementation of 5-HTP and aforesaid alkanoyl L-carnitine or the pharmacologically acceptable salt thereof as active ingredients, or the administration of a combination preparation comprising a mixture of the aforesaid active ingredients, in addition to suitable excipients, if any.

Therefore, the present invention also relates to orally or parenterally administrable pharmaceutical compositions suitable for controlling and decreasing the appetite, which comprise, as active ingredients, 5-HTP and an alkanoyl L-carnitine or a pharmacologically acceptable salt thereof.

Experimental studies have long been conducted in rats, demonstrating the potentiating action of 5-HTP on known anorectic drugs such as amphetamine and fenfluramine (J. Pharm. Pharmac. 1975, 27, 31–37). These studies have been conducted, however, without any intention of assessing the therapeutic effects of 5-HTP in its own right, but simply in order to demonstrate the role of the serotoninergic system in the modulation of alimentary behaviour in rats. To this end, lesions of the hypothalamic structures involved in regulating alimentary habits were induced in the animals and it was found that 5-HTP potentiates the anorexia induced by fenfluramine only in rats with a damaged hypothalamus.

Clearly, the results of these experiments cannot be extrapolated to man. In fact, they offer no indications as to the possible potentiating action of 5-HTP on anorectic agents in man, and are even less demonstrative of an anorectic action of 5-HTP alone or, therefore, of its potential use in human therapy in the absence of well-known anorectics such as amphetamine or fenfluramine.

It is, on the other hand, clearly desirable to have an anorectic agent for human therapy which does not present the well-known unwanted effects typical of amphetamine and fenfluramine or their congeners, ranging from nausea and insomnia to hypertension, cardiac arrhythmias and, in the eventuality of an overdose, even death due to cardiac arrest.

It has now been found that 5-HTP, particularly in combination with an alkanoyl L-carnitine wherein the alkanoyl group has 2–6 atoms, which is, preferably, acetyl L-carnitine exhibits a potent anorectic activity.

There is an obvious advantage to be gained from using 5-HTP in combination with acetyl L-carnitine to induce a state of anorexia for therapeutic purposes in man instead of the above-mentioned anorectics. Indeed, both 5-HTP and acetyl L-carnitine are naturally-occurring substances. Moreover, both 5-HTP and acetyl L-carnitine cross the blood-brain barrier, which is a fundamental prerequisite for their subsequent central pharmacological effect.

5-HTP is the direct precursor of serotonin. Its toxicity is extremely low. Studies conducted in the rat and mouse have demonstrated that the $DL_{50}$ is negligible as compared to therapeutic doses: DL50 per os in the mouse 2500 mg/kg; DL50 i.p. 1400 mg/kg.

A previous use of 5-HTP is known in psychiatry as an adjuvant in nervous, endogenous and involutional depression, and in neurology, as, for instance, in epilepsy, in combination with anticonvulsants, and in Parkinson's disease, in combination with L-dopa.

Also therapeutic uses of acetyl L-carnitine are already known in the treatment of ischemia and myocardial arrhythmias, functional peripheral vascular diseases of the arteries, such as Raynaud's disease and acrocyanosis and the treatment of subjects affected by altered cerebral metabolism which is found for example in senile and pre-senile dementia and in Alzheimer's desease.

However there is no correlation between the previously known therapeutic uses of acetyl L-carnitine and that which forms the subject of this invention.

It is, therefore, an object of the present invention a method for controlling and decreasing the appetite in an overweight individual which comprises administering to said individual an effective amount of 5-hydroxytryptophan and an alkanoyl L-carnitine wherein the alkanoyl group has 2–6 carbons atoms, or a pharmacologically acceptable salt thereof.

Pharmaceutically acceptable salts of alkanoyl L-carnitine include, in addition to the inner salts, all pharmaceutically acceptable salts which are prepared by the addition of acid to an alkanoyl L-carnitine and which do not give rise to undesirable toxic or collateral effects. The formation of pharmaceutically acceptable acid addition salts is well known in the pharmaceutical technology.

Non-limiting examples of suitable salts include the chloride, bromide, iodide, acid aspartate, acid citrate, tartrate, acid phosphate, acid fumarate, glycerophosphate, glucosephosphate, lactate, acid maleate, orotate, acid oxalate, acid sulfate, trichloroacetate, trifluoroacetate, and methansulfonate.

Preferred alkanoyl L-carnitines are those selected from the group consisting of acetyl-, propionyl-, butyryl-, valeryl- and isovaleryl L-carnitine. Acetyl L-carnitine is particularly preferred.

It has been found that it is preferable to administered to an individual in need thereof in a single or multliple regimen dose 5–10 mg/kg/day of 5-hydroxytryptophan and 10–20 mg/kg/day of acetyl L-carnitine or an equivalent amount of a pharmacologically acceptable salt thereof.

The following clinical trial shows the efficacy of the 5-hydroxytryptophan/acetyl L-carnitine treatment for controlling and reducing the appetite in a group of bulimic patients.

CLINICAL TRIAL

A double-blind, placebo-controlled, cross-over clinical trial was conducted. Nineteen bulimic patients suffering from grade-two obesity were recruited into the trial (mean age 41 years; range: 26–52 years). Patients presenting carbohydrate intolerance, dyslipidaemia or abnormal uric acid metabolism were excluded. After giving their informed consent, and after prior randomisation, all patients were submitted, for two consecutive five-week periods, to oral treatment with 5-hydroxytryptophan (HTP) and acetyl L-carnitine (ALC) (8 mg/kg/day of HTP and 12 mg/kg/day of ALC subdivided into three administrations) and placebo. At the end of the first period, the patients who had been on the HTP/ALC treatment then continued on placebo and vice versa.

During the ten-week study period patients were not subjected to dietary restrictions. Body weight was measured and anorexia assessed at one-weekly intervals. Twenty-four-hour urine samples were collected and used for the determination of 5-hydroxy-3-indoleacetic acid (5-HIAA), a terminal catabolite of serotonin turnover, for the purposes of assessing patient compliance at the end of the trial. The urinary 5-HIAA determination was done using S. Udenfried and H. Weissabach's calorimetric method in a 4 ml urine sample (J. Biol. Chem. 216, 449, 1955). At each weekly assessment, patients were asked if they had observed any subjective reduction in appetite. To obtain a more objective definition of the presence of anorexia, patients were invited to reply to a questionnaire aimed at revealing the presence of symptoms such as alterations of taste (AT) and smell (AS), aversion for meat (AM), nausea and/or vomiting (N/V) and early feeling of satiety (EFS), which interfere with food consumption and which may be related to an alteration of the centres involved in the neuroregulation of alimentary behaviour. Patients presenting one or more of the symptoms listed above were considered anorexic.

Patients were submitted on a twice-weekly basis to self-assessment of their feelings of hunger and satiety by means of the Silverstone test. It thus proved possible to assess the patient's anorexia both subjectively and objectively. The data were analysed statistically using Student's t-test for paired data, linear regression analysis and the chi-square test.

RESULTS

In the course of the study the incidence of symptoms responsible for anorexia was significantly greater during the period of 5-HTP/ALC treatment compared to the period of treatment with placebo ($p<0.01$) (see Table IV).

In patients on 5-HTP/ALC, an aversion for meat was present in 27% of cases, alteration of taste in 27% and an early feeling of satiety in 32%. The incidences of these symptoms were lower when taking placebo: for example, an early feeling of satiety was present in 21 % of cases (see Table IV). Over the ten-week study period only one side effect was noted, namely diarrhoea, the percentage incidence of which was higher during treatment with the drug (see Table IV). The self-assessment of feeling of satiety, as evaluated using the Silverstone rating scale, revealed a significant increase in the incidence of this symptom during the period of treatment with 5-HTP/ALC compared to the period of treatment with placebo ($p<0.001$).

Body weight: the mean reduction in body weight of the 19 patients during the 5-HTP/ALC treatment period was greater than the mean reduction in body weight of the same patients during treatment with placebo ($p<0.02$) (see Table II).

5-Hydroxy-3-indoleacetic acid: urinary levels of 5-HIAA in the patients treated with placebo were no different from baseline values (see Table I). By contrast, the 5-HIAA urinary concentrations were significantly increased during 5-HTP/ALC treatment as compared both to pre-study baseline values and to those obtained during placebo treatment ($p<0.001$) (see Table I).

TABLE I

Mean urinary concentration of 5-hydroxy-3-indoleacetic acid during the period of treatment with 5-HTP/ALC compared to mean urinary concentration during the period of treatment with placebo (the mean baseline urinary concentration of 5-hydroxy-3-indoleacetic acid prior to the start of the trial was 9.83 ± 4.55 mg/24 h)

|  | Week 1 | Week 2 | Week 3 | Week 4 | Week 5 |
| --- | --- | --- | --- | --- | --- |
| Placebo | 9.97 ± 4.94 | 9.60 ± 5.20 | 10.65 ± 3.88 | 7.59 ± 3.33 | 8.82 ± 4.36 |
| 5-HTP/ALC | 238.57 ± 95 | 211.12 ± 93.74 | 245.47 ± 53.44 | 209 ± 52.73 | 182.48 ± 50.22 |
|  | p < 0.001 | p < 0.001 | p < 0.001 | p < 0.001 | p < 0.001 |

Mean basal vs mean placebo  n.s.
Mean basal vs mean 5-HTP  p < 0.001
Mean placebo vs mean 5-HTP  p < 0.001

TABLE II

Body weight reduction compared to treatment with placebo (mean ± s.e.).

| | |
| --- | --- |
| Mean body weight reduction (in grams) during the 5-week treatment with placebo | −420 ± 356 |
| Mean body weight reduction (in grams) during the 5-week treatment with 5-HTP/ALC | −1420 ± 425 | p < 0.02

TABLE III

Self-assessment of appetite and satiety using the Silverstone rating scale.

|  | APPETITE | SATIETY |
| --- | --- | --- |
| PLACEBO | 7.07 ± 3.53 | −21.6 ± 3.25 |
|  | N.S. | t = −13.4 p<0.001 |
| 5-HTP/ALC | 7.90 ± 3.21 | −35.5 ± 3.14 |

Mean value of 19 subjects during treatment with placebo and with 5-HTP/ALC.

TABLE IV

| SYMPTOM | PLACEBO | 5-HTP/ALC | $X^2$ |
|---|---|---|---|
| Alteration of taste | 0(0) | 27.31%(5) | <0.05 |
| Alteration of smell | 0(0) | 0(0) | n.s. |
| Aversion for meat | 0(0) | 27.31%(5) | <0.05 |
| Early sense of satiety | 21.05%(4) | 31.57%(6) | n.s. |
| Anorexia* | 31.57%(6) | 78.94%(15) | <0.01 |
| Side effects | | | |
| Diarrhoea | 10.52%(2) | 42.10%(8) | n.s. |
| Total symptoms presented during trial | 42.10%(8) | 78.94%(15) | <0.05 |

*Defined as presence of at least one of the symptoms listed above.

The anorectic compositions of the present invention comprise 5-hydroxytryptophan and an alkanoyl L-carnitine wherein the alkanoyl group has 2–6 carbon atoms or a pharmacologically acceptable salt thereof as active ingredients and a pharmacologically acceptable excipient. The compositions wherein the alkanoyl L-carnitine is acetyl L-carnitine or a pharmacologically acceptable salt thereof are particularly preferred.

Such compositions in unit dosage form generally comprise 100–200 mg of 5-hydroxytryptophan and 250–500 mg of acetyl L-carnitine or an equivalent molar amount of a pharmacologically acceptable salt thereof.

For preparing the anorectic compositions of the present invention, 5-HTP and ALC can be formulated in the same pharmaceutical forms as those which are known to be used in psychiatry and neurology for administering separately each individual active ingredient.

For instance, capsules, sachets and granulates are suitable forms for oral administration. The following is a suitable composition for capsules:

| 5-HTP | 250 mg |
|---|---|
| ALC | 350 mg |
| amide | 20 mg |
| mannitol | 30 mg |
| magnesium stearate | 3 mg |

These pharmaceutical forms allow the effective doses of 5-HTP and ALC to be administered comfortably and with optimal compliance.

What is claimed is:

1. A method for controlling and decreasing the appetite in an overweight individual which comprises administering to said individual an effective amount of 5-hydroxytryptophan and an alkanoyl L-carnitine wherein the alkanoyl group has 2–6 carbons atoms, or a pharmacologically acceptable salt thereof.

2. The method of claim 1, wherein the alkanoyl L-carnitine is selected from the group consisting of acetyl-, propionyl-, butyryl-, valeryl- and isovaleryl L-carnitine.

3. The method of claim 2, wherein the alkanoyl L-carnitine is acetyl L-carnitine.

4. The method of claim 3 which comprises administering to said individual in a single or multiple dose administration regimen 5–10 mg/kg/day of 5-hydroxytryptophan and 10–20 mg/kg/day of acetyl L-carnitine or an equivalent amount of a pharmacologically acceptable salt thereof.

5. The method of claim 1, wherein the pharmacologically acceptable salt of acetyl L-carnitine is selected from the group consisting of acetyl L-carnitine chloride, bromide, iodide, acid aspartate, acid citrate, tartrate, acid phosphate, acid fumarate, glycerophosphate, glucosephosphate, lactate, acid maleate, orotate, acid oxalate, acid sulfate, trichloroacetate, trifluoroacetate, and methansulfonate.

6. The method of claim 1, wherein said individual is a human.

* * * * *